United States Patent [19]

Franczyk

[11] Patent Number: 5,367,112
[45] Date of Patent: Nov. 22, 1994

[54] PROCESS TO PREPARE AMINO CARBOXYLIC ACID SALTS

[75] Inventor: Thaddeus S. Franczyk, Maryland Heights, Mo.

[73] Assignee: Monsanto Company, St. Louis, Mo.

[21] Appl. No.: 165,793

[22] Filed: Dec. 13, 1993

Related U.S. Application Data

[63] Continuation-in-part of Ser. No. 44,682, Apr. 12, 1993, Pat. No. 5,292,936.

[51] Int. Cl.$^5$ .................... C07C 51/00; C07C 51/097
[52] U.S. Cl. ..................... 562/526; 562/539; 562/553; 562/572
[58] Field of Search ............... 562/526, 539, 553, 572

[56] References Cited

U.S. PATENT DOCUMENTS

| | | | |
|---|---|---|---|
| 3,997,478 | 12/1976 | Petro | 252/470 |
| 4,782,183 | 11/1988 | Goto et al. | 562/526 |
| 4,810,426 | 3/1989 | Fields et al. | 260/502.5 |
| 5,220,055 | 6/1993 | Urano et al. | 562/526 X |
| 5,225,592 | 7/1993 | Gomez et al. | 562/526 |

FOREIGN PATENT DOCUMENTS

WO92/06069 3/1992 WIPO.

OTHER PUBLICATIONS

Laine et al. "Structure and Activity of Chromium-Promoted Raney Copper Catalysts for Carbon Monoxide Oxidation", *Applied Catalysis*, 44 (1988) pp. 11–22.

Anonymous "Improved Process for Producing Aminocarboxylic Acid Salt", No. 35437, *Research Disclosure* (Oct. 1993).

*Primary Examiner*—Arthur C. Prescott
*Attorney, Agent, or Firm*—Frank D. Shearin

[57] ABSTRACT

An improved process is disclosed to prepare an carboxylic acid salt. According to the process, an aqueous solution of an alcohol is contacted with an alkali metal hydroxide in the presence of an effective amount of a copper catalyst that contains from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof. Raney copper is preferred.

10 Claims, No Drawings

PROCESS TO PREPARE AMINO CARBOXYLIC ACID SALTS

CROSS REFERENCES TO RELATED APPLICATIONS

This application is a continuation in part of application Ser. No. 08/044,682 filed Apr. 12, 1993 now U.S. Pat. No. 5,292,936.

BACKGROUND OF THE INVENTION

This invention relates to the preparation of carboxylic acid salts, and more particularly, relates to a method for the preparation of carboxylic acid salts by the reaction of primary alcohols with an alkali metal hydroxide in the presence of a copper catalyst.

Carboxylic acid salts are useful in various applications. The salts can be neutralized to the corresponding acid which is also useful in a number of applications, such as a raw material for pharmaceuticals, agricultural chemicals and pesticides. Many of such carboxylic acids are available commercially in large quantities.

U.S. Pat. No. 4,782,183 to Goto et al. discloses a method for the manufacture of amino carboxylic acid salts which comprises subjecting an amino alcohol to an alkali metal hydroxide in the presence of a Raney copper catalyst.

In a patent application published by WIPO as WO 92/06069 on Apr. 16, 1992, a process is disclosed for producing glycine, iminodiacetic acid and nitrilotriacetic acid salts by contacting monoethanolamine, diethanolamine or triethanolamine with an alkali metal hydroxide in the presence of a Raney copper catalyst, wherein at least some of the Raney copper catalyst has been rejuvenated by treating the catalyst under reflux conditions with formic acid (attorney docket No. 39-21 (3145)).

A journal article "Structure and Activity of Chromium-Promoted Raney Copper Catalyst for Carbon Monoxide Oxidation" by Laine et al., *Applied Catalysis*, 44 (1-2), pages 11-22, discloses that chromium-promoted Raney copper catalysts were prepared, and their activity for the oxidation of carbon monoxide was measured. The surface area of the Raney copper catalyst was directly related to the aluminum content in the precursor alloy and to a lesser extent to the presence of chromium. Bulk cuprous oxide and cupric oxide were detected by X-ray diffraction in the Raney copper catalyst. The presence of chromium inhibited the formation of cupric oxide but not of cuprous oxide. The activity decreased as chromium content increased.

U.S. Pat. No. 4,810,426 to Fields et al., discloses a process for the production of N-phosphonomethylglycine by oxidizing N-phosphonomethylethanolamine or the cyclic internal ester thereof with an excess of an aqueous alkali and a copper catalyst, and thereafter heating at a temperature between 200° and 300° C. Thereafter, the salt is neutralized with an acid to produce the desired N-phosphonomethylglycine.

Although satisfactory results are achieved by the processes of the prior art to convert an alcohol to a carboxylic acid using a copper catalyst, or even a Raney copper catalyst, it has been found that upon repeated usage of the copper catalyst, the activity of the catalyst decreases. Now, it has been found, in accordance with the teachings of the present invention, that the activity of the Raney copper catalyst can be extended to a significant degree, permitting more economic utilization of the catalyst, to convert any number of alcohols to the corresponding carboxylic acid.

SUMMARY OF THE INVENTION

These and other advantages are achieved in a process to manufacture a carboxylic acid salt which comprises contacting an aqueous solution of a primary alcohol with an alkali metal hydroxide in the presence of an effective amount of a copper catalyst containing from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof.

DETAILED DESCRIPTION OF THE INVENTION

The primary alcohols which are useful as starting materials in the process of the present invention can be aliphatic, cyclic or aromatic, and are those known to those skilled in the art. It is only necessary that the alcohol and the resulting carboxylate are stable in the hot caustic solution, and that the alcohol is somewhat water soluble. Suitable primary alcohols include aliphatic alcohols having from 2 to about 20 carbon atoms, and preferably from 2 to about 10 carbon atoms since the reaction to convert an alcohol containing more than 10 carbon atoms to the corresponding acid may be slower as the number of carbon atoms increases. The aliphatic portion of the alcohol can be branched, straight chain, or cyclic, and can be substituted with various groups, provided that the groups do not react with the alkali metal hydroxide or the copper catalyst at the temperatures and pressures of the conversion of the alcohol to the acid. Suitable aliphatic alcohols include ethanol, propanol, butanol, pentanol, and the like.

Amino alcohols represented by the formula

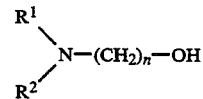

are also useful as starting materials in the present process where n is 2 to 20. When $R^1$ and $R^2$ are both hydrogen, the amino alcohol is monoethanolamine. When one of $R^1$ and $R^2$ is —$CH_2CH_2OH$ or —$CH_2COOH$, and the other R group is hydrogen, the resulting product from amino alcohol would be an iminodiaceto salt. When both $R^1$ and $R^2$ are —$CH_2CH_2OH$ or —$CH_2COOH$, the resulting product from the amino alcohol would be nitrilotriacetic acid.

In the above formula, $R^1$ and/or $R^2$ can also be an alkyl group having from 1 to 6 carbon atoms, for example, methyl, ethyl, propyl, isopropyl, butyl, isobutyl and the like. There would then be provided corresponding amino acids with these alkyl groups which would be useful in a number of applications. $R^1$ or $R^2$ can also be a phosphonomethyl group such that the starting amino acid would be N-phosphonomethylethanolamine, and the resulting amino acid would be N-phosphonomethylglycine. If one of $R^1$ or $R^2$ were phosphonomethyl, and the other were —$CH_2CH_2OH$, the resulting amino acid would be N-phosphonomethyliminodiacetic acid, which can be converted to N-phosphonomethylglycine by any number of techniques known to those skilled in the art. If one of $R^1$ or $R^2$ were phosphonomethyl, and the other were an alkyl group, the resulting amino acid would be an N-alkyl-N-phosphonomethylglycine which could be converted to N-phosphonomethylglycine by the teachings in U.S. Pat. No. 5,068,404 to Miller and Balthazor.

The copper catalysts of the present invention can be prepared by techniques known to those skilled in the art. For example, an aqueous solution of a copper salt can be reduced to provide a finely divided copper metal, which can then be treated with a salt of an element selected from the group consisting of chromium, titanium, niobium, tantalum, zirconium, vanadium, molybdenum, manganese, tungsten, cobalt, nickel and mixtures thereof. On the other hand, the salt of the above elements can be reduced and co-precipitated with the copper metal from the aqueous solution, and this is preferred.

Raney copper catalysts, which are especially preferred, can be prepared by techniques known to those skilled in the art from alloys containing copper and aluminum, and thereafter, the aluminum is leached from the alloy with an aqueous alkali metal hydroxide to provide an activated Raney copper. The activated Raney copper can then be treated with a nitrate, sulfate or other salt of an element selected from the group consisting of chromium, titanium, niobium, tantalum, zirconium, vanadium, molybdenum, manganese, tungsten, cobalt, nickel and mixtures thereof, but it is preferred to incorporate the above elements into the copper aluminum alloy during the preparation of the Raney copper. Of the above elements, chromium, molybdenum, and mixtures of chromium and molybdenum are preferred.

The amount of added element in the copper can vary within wide limits. Improved results for the conversion of an alcohol to an acid can be seen with as little as 50 parts per million added element in the copper. As an upper limit, the copper can contain up to about 10,000 parts per million added element, and the Raney copper can even contain higher levels, although such higher levels do not provide significantly improved results for the conversion of the alcohol to the corresponding acid. It is preferred to use a copper catalyst having a content of added element between about 50 and 5000 parts per million.

The amount of catalyst to be used to convert the alcohol to the corresponding acid can range between about 1% and about 70% by weight, preferably 10 to 40% by weight based on the amount of the starting alcohol. The catalyst can generally be used repeatedly in the reaction for a greater number of times than a copper catalyst without the added element.

The alkali metal hydroxides for use in the process of the present invention include lithium hydroxide, sodium hydroxide, potassium hydroxide, rubidium hydroxide and cesium hydroxide. The amount of the hydroxide of the alkali metal to be used is an equivalent amount in the range of 1.0 to 2.0 equivalents relative to the hydroxyl group of the alcohol to be used in the reaction. The hydroxide can be in the form of flakes, powder, pellets or an aqueous solution. Because of their ready availability and ease of handling, sodium hydroxide and potassium hydroxide are preferred, and sodium hydroxide is especially preferred.

In the process of the present invention, it is only necessary to contact the alcohol with an alkali metal hydroxide in the presence of the copper catalyst containing about 50 parts per million to about 10,000 parts per million of the added element at a temperature between about 120° C. and 220° C., preferably between about 140° C. and about 200° C. At temperatures above about 220° C., the Raney copper catalyst begins to lose selectivity. At temperatures below about 120° C., satisfactory results can be obtained, but the reaction is slow.

Pressure is required for the reaction to proceed at the temperatures indicated above. However, the reaction pressure is desired to be as low as possible to insure high reaction velocity. Generally, it is necessary to exceed the minimum pressure at which the reaction proceeds in the liquid phase, preferably between 5 and about 30 kg/cm$^2$, preferably in the range of 5 to 20 kg/cm$^2$. The conversion of the alcohol to the corresponding salt of the acid proceeds with the liberation of hydrogen, which should be vented with care from the reaction vessel.

The invention is further illustrated by, but not limited to, the following examples:

EXAMPLE 1

This example illustrates the results that are obtained using a copper catalyst without chromium an added element.

Into a 300 ml nickel autoclave equipped with a stirrer was charged diethanolamine (62.5 g, 0.59 mol.) water (60 ml) and a 50% aqueous solution of sodium hydroxide (50 g NaOH, 1.25 mol.) Then, a Raney copper catalyst (12.4 g) was added to the autoclave. The autoclave was sealed, and heated to a temperature of 160° C. under a pressure of 9.5 Kg/cm$^2$ while stirring the liquid phase in the autoclave. Heating was continued until hydrogen gas was no longer evolved, indicating that the reaction was complete. The reaction time was recorded, and the catalyst was reused in a subsequent run. In all cases the yield of iminodiacetic acid was about 95%. The results are shown in Table 1.

TABLE 1

| Reaction Times for Repeated Use of the Same Raney Copper Catalyst | |
|---|---|
| Cycle | Reaction Time (hours) |
| 1 | 4.0 |
| 2 | 5.2 |
| 3 | 4.8 |
| 4 | 5.2 |
| 5 | 5.9 |
| 6 | 6.5 |
| 7 | 7.0 |
| 8 | 7.2 |
| 9 | 8.0 |

EXAMPLE 2

This example illustrates the use of a copper catalyst containing chromium according to the present invention.

The procedure of Example 1 was repeated except that a Raney copper catalyst containing 943 parts per million chromium was used in 25 cycles of the catalyst. The results are shown in Table 2.

TABLE 2

| Reaction Times for Repeated Use of a Chromium Promoted Raney Copper Catalyst | |
|---|---|
| Cycle | Reaction Time (hours) |
| 1 | 5.8 |
| 2 | 6.7 |

TABLE 2-continued

Reaction Times for Repeated Use of a
Chromium Promoted Raney Copper Catalyst

| Cycle | Reaction Time (hours) |
|---|---|
| 3 | 6.6 |
| 4 | 6.2 |
| 5 | 6.4 |
| 6 | 6.3 |
| 7 | 6.0 |
| 8 | 6.0 |
| 9 | 6.0 |
| 10 | 6.2 |
| 15 | 7.0 |
| 20 | 7.0 |
| 25 | 8.0 |

A comparison of the data in Table 1 and Table 2 shows that the reaction times for the Raney copper catalyst containing chromium is longer for about the first five cycles, but remains relatively steady for an additional 20 cycles. The reaction time at cycle 25 is 8 hours, whereas a reaction of 8 hours was reached after only 9 cycles using a standard Raney copper catalyst (Table 1).

EXAMPLE 3

This example illustrates the use of a Raney copper catalyst treated with chromic nitrate prior to its first use to convert diethanolamine to the disodium salt of iminodiacetic acid according to the present invention.

Into a 50 ml beaker is placed activated Raney copper (4.13 g), water (10 ml) and chromic nitrate (0.50 g of 15 weight % Cr (NO$_3$)$_3$, 4,000 ppm Cr based on the total mass of copper), and the mixture is allowed to stand 15 minutes. The Raney copper and the supernatant are transferred to a 160 ml nickel autoclave along with diethanolamine (21.2 g, 0.20 mol.) water (10 ml) and a 50% aqueous solution of sodium hydroxide (19 g NaOH, 0.42 mol.). The autoclave is sealed, and heated to 160° C. under 9.5 Kg/cm$^2$ pressure while stirring the liquid phase in the autoclave. Heating is continued until hydrogen gas is no longer evolved, indicating that the reaction is complete. The reaction time is recorded and the catalyst is reused without further addition of chromium. The results are shown in Table 3.

TABLE 3

Reaction Times for Raney Copper
Catalyst Prepared by Adding Chromium Nitrate

| Cycle | Reaction Time (hours) |
|---|---|
| 1 | 4.0 |
| 2 | 3.5 |
| 3 | 3.5 |
| 4 | 3.1 |
| 5 | 2.7 |
| 6 | 2.7 |
| 7 | 2.7 |
| 8 | 2.7 |
| 9 | 2.7 |
| 10 | 2.7 |
| 11 | 3.0 |
| 12 | 2.8 |
| 13 | 3.1 |
| 14 | 3.1 |
| 15 | 3.2 |

As the data in Table 3 indicates, reaction times improve over the first 4 cycles, and then remains relatively constant, ranging from 2.7 to 3.2 hours for the remaining cycles. Using untreated Raney copper as the catalyst, only the first cycle falls within a 2.7-3.1 hour reaction time, and subsequent cycles require progressively longer periods (eg., 3.5 to 7 hours) to reach endpoint.

EXAMPLE 4

This example illustrates the use of a copper catalyst containing chromium to convert N-2-(hydroxyethyl)aminomethylphosphonic acid to N-phosphonomethylglycine.

Into a 160 ml nickel autoclave equipped with a stirrer is charged N-2-(hydroxyethyl)aminomethylphosphonic acid (16.84 g, 0.11 mol.) water (11.3 ml) and 45 weight % potassium hydroxide (48.7 g, 0.39 mol.) and Raney copper catalyst containing 943 parts per million chromium (3.53 g). The autoclave is sealed and heated to 160° C. under a pressure of 9.5 Kg/cm$^2$ while stirring the liquid phase in the autoclave. After 1.85 hours, hydrogen evolution ceases. The yield of N-phosphonomethylglycine as its potassium salt is 98.5%.

EXAMPLE 5

This example illustrates the conversion of N-phosphonomethyl-2-oxazolidone to N-phosphonomethylglycine using a copper catalyst containing chromium.

The procedure of Example 4 is repeated except that N-phosphonomethyl-2-oxazolidone made by the process described in U.S. Pat. No. 4,547,324 is used instead of N-2(hydroxyethyl)aminomethylphosphonic acid. After 2 hours of heating, the yield of N-phosphonomethylglycine is 86.2% as determined by HPLC analysis.

EXAMPLE 6

This example illustrates the conversion of diethanolamine to disodium iminodiacetate using a copper catalyst containing molybdenum.

The procedure of Example 1 was repeated except that a Raney copper catalyst containing about 500 parts per million molybdenum was used in 12 cycles of the catalyst. After each cycle 2.5 percent of the Raney copper was replaced with fresh catalyst. The results are shown in Table 4.

TABLE 4

Reaction Times for Raney Copper
Catalyst with Added Molybdenum

| Cycle | Reaction Time (hours) |
|---|---|
| 1 | 3.1 |
| 2 | 3.6 |
| 3 | 3.5 |
| 4 | 3.9 |
| 5 | 4.2 |
| 6 | 4.5 |
| 7 | 4.7 |
| 8 | 4.9 |
| 9 | 5.0 |
| 10 | 5.2 |
| 11 | 5.4 |
| 12 | 5.5 |

As can be seen by comparing the reaction times in Table 4 with the reaction times in Table 1, the Raney copper containing molybdenum provided faster reactions than Raney copper without the added molybdenum. In addition, there was no adverse effect on selectivity, i.e., no increased levels of unwanted byproducts.

EXAMPLE 7

The procedure of Example 6 is repeated except that the Raney copper contains about 500 ppm chromium and 500 ppm molybdenum. Substantially the same results are obtained.

EXAMPLE 8

The procedure of Example 2 is repeated in a series of tests using Raney copper containing titanium, zirconium, niobium, tantalum, vanadium, manganese, tungsten, cobalt or nickel. In each of these tests the results are not as good as the results obtained in Example 2, but are better than the results obtained in Example 1. In the experiments using a Raney copper catalyst containing various amounts of vanadium, the best results were obtained when the level of vanadium in the Raney copper was between about 50 ppm and about 200 ppm.

EXAMPLE 9

This example illustrates the use of a Raney copper catalyst containing molybdenum to convert 3-aminopropanol to sodium 3-aminopropionate.

A mixture consisting of 3-aminopropanol, (49.80 g, 0.663 mol), a 61.20 g slurry of Raney copper in water (50 ml total volume, 12.61 g Cu, 60 ppm Mo), 50 w/w% NaOH (56.9 g, 0.711 mol), and 25 g deionized water was charged to a 300 ml nickel Parr reactor equipped with a stirrer, a gas regulator to maintain constant back pressure, and a Porter hydrogen mass flow indicator interfaced with an IBM computer. Heating to 160° C. induced rapid (>600 cc/min) hydrogen evolution that ceased after 1.5 hours. Analysis of the filtered product mixture by NMR was consistent with a 85:15 ratio of sodium 3-aminopropionate and sodium propionate, respectively.

EXAMPLE 10

This example illustrates the use of a copper catalyst containing molybdenum to convert an aromatic alcohol to the corresponding acid salt.

A mixture containing benzyl alcohol (62.59 g, 0.579 mol), 61.45 g of a Raney copper slurry in water (50 cc total volume, 12.89 g copper, 60 ppm Mo), 50 w/w% NaOH (50.34 g, 0.629 mol), and 24 g deionized water was charged to the rector described in Example 9. Heating to 160° C. yielded slow evolution of hydrogen (~50 cc/min). After 30 min. the temperature was increased to 170° C. to speed conversion. After a total of 13 hours at 160° C., hydrogen evolution ceased and the filtered reaction mixture was analyzed by NMR. The $^1$H and $^{13}$C NMR spectra obtained from the product was consistent with that of sodium benzoate. An aliquot of the product mixture was acidified with HCl and recrystallized from water to afford white plates: m.p. 121°–122° C. (lit. m.p. 122.4° C.).

EXAMPLE 11

This example illustrates the use of a copper catalyst containing molybdenum to convert a polyol to the corresponding acid.

The reactor of Example 9 was charged with ethylene glycol (30.27 g, 0.487 mol), a 61.66 g slurry of Raney copper in water (50 cc total volume, 13.12 g copper, 60 ppm Mo), 50 w/w% NaOH (39.77 g, 0.497 mol), and 70 g of deionized water. The mixture was heated to 160° C. with rapid evolution of hydrogen (>600 cc/min). After 1.5 hours, hydrogen evolution ceased. Analysis of the filtered reaction mixture by HPLC revealed a 93% yield consisting of about 90 mol% sodium glycolate and 10 mol% sodium oxalate.

In another run the reactor was charged with ethylene glycol (30.40 g, 0.490 mol), a 61.76 g slurry of the Raney copper in water (50 cc total volume, 13.24 g copper), and 45.8 w/w% KOH (128.13 g, 1.05 mol). The reaction mixture was heated to 160° C. and the evolution of hydrogen was initially rapid (>600 cc/min). After about 45 minutes, hydrogen evolution slowed to about 30 cc/minute where it decayed slowly with time. The reaction was manually terminated after 20 hours at >160° C. Analysis of the filtered reaction mixture by HPLC revealed a yield of 25 mol% potassium glycolate and 75 mol% potassium oxalate.

EXAMPLE 12

This example illustrates the use of a Raney copper catalyst containing molybdenum to convert glycolic acid to sodium oxalate.

Into a 300 ml Hastelloy C-276 autoclave (Parr Instrument Co.) equipped with a stirrer was added diethanolamine (62.44 g, 0.59 mole), 50% aqueous sodium hydroxide solution (99.90 g, 1.24 mol), glycolic acid (1.35 g, 17.75 mmol), and Raney copper containing 60 ppm molybdenum (12.49 g, 0.20 mol). Water was added to adjust the total weight to 256.00 g and the autoclave was then sealed. The autoclave was purged with nitrogen, pressurized to 9.49 kg/cm$^2$ and heated to 160° C. with stirring. The reaction was stopped when the off gas flow rate was at 3.5 ml/min (5.8 hours). The autoclave was cooled to 80° C. and the contents were filtered and rinsed with water. In addition to the expected product, disodium iminodiacetate, analysis showed that the reaction mixture also contained sodium glycolate (2.27 mole-%) and disodium oxalate (1.38 mole%) based on the moles of diethanolamine used. These data represents a 30% conversion of glycolic acid to disodium oxalate under these reaction conditions.

EXAMPLE 13

This example illustrates the conversion of cinnamyl alcohol to an acid.

Into a 300 ml nickel autoclave was charged cinnamyl alcohol (50.0 g, 0.373 mol), sodium hydroxide (34.59 g, 0.432 mol) Raney copper containing about 70 ppm molybdenum (12.81 g copper suspended in 48.6 g water) and water (75 g). The autoclave was sealed and purged with nitrogen. The autoclave was heated under pressure to 170° C. for about 18 hours. The reaction products were filtered and the basic filtrate was extracted with diethyl ether. The aqueous phase was acidified and extracted with ether. The acid and base extracts were evaporated and analyzed. The reaction yielded 3-phenylpropionate (69%), 3-phenylpropanol (25%) and benzoate (8%) with 96% closure.

Although the invention has been described in terms of specified embodiments which are set forth in considerable detail, it should be understood that this is by illustration only, since alternative embodiments and operating techniques will become apparent to those skilled in the art in view of the disclosure. For example, any number of carboxylic acids other than those described herein can be prepared by the conversion of the corresponding alcohol using the copper catalyst containing an added element in accordance with the teachings of the present invention. Accordingly, modifications can be made without departing from the spirit of the described invention.

What is claimed is:

1. A process to manufacture carboxylic acid salt which comprises contacting an aqueous solution of a primary alcohol with an alkali metal hydroxide in the presence of an effective amount of a copper catalyst containing from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof.

2. A process of claim 1 wherein the copper catalyst is Raney copper.

3. A process of claim 1 or claim 2 wherein the copper catalyst contains from about 50 parts per million to about 5000 parts per million chromium.

4. A process of claim 1 or claim 2 wherein the copper catalyst contains from about 50 parts per million to about 5,000 parts per million molybdenum.

5. A process of claim 2 wherein the Raney copper catalyst contains from about 50 parts per million to about 5,000 parts per million chromium and from about 50 parts per million to about 5,000 parts per million molybdenum.

6. A process of claim 1 wherein the alcohol is an aromatic alcohol.

7. A process of claim 6 wherein the alcohol is benzyl alcohol.

8. A process of claim 1 wherein the alcohol is an aliphatic alcohol having from 2 to about 20 carbon atoms.

9. A process of claim 8 wherein the alcohol has from 2 to about 10 carbon atoms.

10. A process of claim 1 wherein the alcohol is a polyol.

* * * * *